United States Patent
Schultz

(10) Patent No.: US 10,736,708 B2
(45) Date of Patent: Aug. 11, 2020

(54) DISPENSING CARTRIDGE FOR TACKING NAILS FOR ATTACHING MEDICAL-GRADE FILMS TO BONES

(71) Applicant: Rodenbacher Chaussee 4, Hanau (DE)

(72) Inventor: Geraldine Schultz, Malsch (DE)

(73) Assignee: Dentsply Implants Manufacturing GmbH, Hanau (DE)

(*) Notice: Subject to any disclaimer, the term of this patent is extended or adjusted under 35 U.S.C. 154(b) by 154 days.

(21) Appl. No.: 15/772,283

(22) PCT Filed: Aug. 30, 2016

(86) PCT No.: PCT/EP2016/001461
§ 371 (c)(1),
(2) Date: Apr. 30, 2018

(87) PCT Pub. No.: WO2017/071786
PCT Pub. Date: May 4, 2017

(65) Prior Publication Data
US 2018/0310932 A1    Nov. 1, 2018

(30) Foreign Application Priority Data

Oct. 30, 2015    (DE) .................. 10 2015 118 645

(51) Int. Cl.
*A61B 50/30*    (2016.01)
*A61C 19/02*    (2006.01)
(Continued)

(52) U.S. Cl.
CPC .......... *A61B 50/30* (2016.02); *A61B 17/0642* (2013.01); *A61B 17/07207* (2013.01);
(Continued)

(58) Field of Classification Search
CPC .. A61B 17/846; A61B 50/30; A61B 17/07207
See application file for complete search history.

(56) References Cited

U.S. PATENT DOCUMENTS 4,606,455 A * 8/1986 Grikis .................... F16B 27/00
                                                         206/347
5,741,268 A    4/1998 Schutz
(Continued)

FOREIGN PATENT DOCUMENTS

| DE | 10 2014 003 398 A1 | 9/2015 |
| EP | 0733346 A1 | 9/1996 |
| EP | 0867193 A2 | 9/1998 |

OTHER PUBLICATIONS

International Preliminary Report on Patentability for PCT/EP2016/001461, dated May 11, 2018.
(Continued)

*Primary Examiner* — Andrew Yang
(74) *Attorney, Agent, or Firm* — Katterle Nupp LLC; Paul Katterle; Robert Nupp

(57) ABSTRACT

A dispensing cartridge is provided for holding one or more tacking nails for attaching medical-grade films to bones. The cartridge includes a base body having a plateau area with a plurality of grooved depressions formed therein. Slotted openings extend through the grooved depressions and are adapted for holding a plurality of the tacking nails. A gripping area is disposed adjacent to the plateau area and is provided with knob-like or wavy elevations. A support area is disposed underneath the plateau area and provides support to the base body. A transparent plastic layer may be disposed over and conform to the base body of the dispensing cartridge so as to form a plastic package.

17 Claims, 6 Drawing Sheets

(51) Int. Cl.
*A61B 17/84* (2006.01)
*A61B 17/072* (2006.01)
*A61B 17/064* (2006.01)
*A61C 8/00* (2006.01)

(52) U.S. Cl.
CPC ........ *A61B 17/846* (2013.01); *A61B 50/3001* (2016.02); *A61C 19/02* (2013.01); *A61B 2017/0647* (2013.01); *A61B 2050/3008* (2016.02); *A61C 8/0089* (2013.01)

(56) References Cited

U.S. PATENT DOCUMENTS

| | | |
|---|---|---|
| 6,402,759 B1 | 6/2002 | Strong et al. |
| 2002/0121539 A1 | 9/2002 | Strong et al. |

OTHER PUBLICATIONS

International Search Report for PCT/EP2016/001461, dated Feb. 28, 2017.

\* cited by examiner

DISPENSING CARTRIDGE FOR TACKING NAILS FOR ATTACHING MEDICAL-GRADE FILMS TO BONES

CROSS-REFERENCE TO RELATED APPLICATION(S)

This application is the U.S. national phase of PCT Application No. PCT/EP2016/001461 filed on Aug. 30, 2016, which claims priority to German Patent Application No. 10 2015 118 645.4 filed on Oct. 30, 2015, the disclosures of which are incorporated in their entirety by reference herein.

TECHNICAL FIELD

The disclosure relates to a dispensing cartridge for tacking nails for attaching medical-grade films to bones, in particular membrane films for covering bone defects in jawbones.

BACKGROUND

When using dental implants in the jawbones of dental patients, an opening is first introduced into the jawbone, into which the implant body is inserted, e.g., screwed in with a corresponding threaded section. After the implant body has been inserted, the wound opening formed in the jawbone and overlying gums is temporarily closed by a cover film that acts as a membrane to heal the implant body, which for example consists of titanium, and protects the opening against a detachment of tissue cells and penetration of soft tissue, while simultaneously allowing an exchange of material between the wound opening and oral cavity. For example, such a cover film, which is also referred to as a membrane film in the present application, is known from EP 0 867 193 B1.

In order to here attach the membrane film to the jawbone over the wound opening, it is fixed in place with tacking nails, which exhibit a shank extending from the nail head to the nail tip, followed by a thickened area that acts as a barb after the nail has been driven through the film and into the jawbone. Also referred to below as membrane nails, such tacking nails along with the accompanying positioning instrument for driving the latter into a jawbone are described in EP 0 733 346 A1, for example.

During insertion of the membrane nails, the problem here becomes that the latter must be gripped by the nail head with the positioning element, and pressed into the receiving head of the tool by exerting a certain level of force. In order to prevent the danger of infection in the oral cavity as much as possible while placing the membrane nails, the nails must as far as possible only come into contact with objects and tools that were sterilized beforehand. This makes handling the nails during transport to the dentist as well as inserting them into the positioning instruments comparatively complicated, and generally requires another assistant to help the dentist remove the nails from a sterile transport package and subsequently insert them into the positioning instrument.

To this end, the nails are transported in special metal dispensers, into which separate holes are introduced from above, into which nails are individually inserted, so that the latter can be gripped with the insertion instrument on the nail head, and pulled out of the hole in the vertical direction.

In this conjunction, the applicant uses a dispensing device molded in a strip-shaped base body consisting of plastic material, wherein the latter is then inserted into a glass tube. The problem here arises that the nail heads protrude over the top side and bottom side of the strip-shaped base body, since the latter only exhibits a height less than the length of the nail. Another problem associated with the aforementioned dispensing device is that the base body for accommodating a nail cannot be placed on a substrate given the lack of any suitable support surface on the bottom side, but must rather be freely held by the dentist or a second person when the positioning element is pressed onto the nail head so as to mechanically snap the latter into the positioning device. Since the forces necessary for snapping the nails in are sometimes quite significant, the danger here is that the positioning device will slide off, and the base body with the nails accommodated therein will inadvertently come into contact with unsterilized objects, or even with body parts.

Accordingly, it would be desirable to provide a dispensing cartridge for tacking nails for attaching medical films to bones, in which a plurality of tacking nails can be transported and stored without contact with external package parts, and which enables a sterile and easy removal of the tacking nails by means of a positioning instrument.

SUMMARY

Accordingly, the present disclosure describes a dispensing cartridge for holding one or more tacking nails for attaching medical films to bones. Each tacking nail includes an expanded nail head, a nail shank extending away from the nail head, and an expanded arrowhead-like area adjacent thereto, which tapers to a tip. The dispensing cartridge includes a base body in which at least one slotted opening is formed, into which the nail with its nail shank may be inserted. The base body has a gripping area and a plateau area adjacent thereto. The slotted opening is formed in the plateau area and has a width that is smaller than the diameter of the nail shank, so that the nail shank may be fixedly clamped in the slotted opening. A grooved depression extending on either side of the slotted opening is formed on a top side of the plateau area. The grooved depression has a depth that is greater than a height of the nail head and a width that is greater than a diameter of the nail head. A support area is disposed underneath the plateau area. The base body is supported against the support area when a compressive force is applied to the nail head of the tacking nail that has been inserted into the slotted opening.

Also provided in accordance with the disclosure is a plastic package that is impervious to germs and resistant to gamma rays. The package includes the dispensing cartridge described above and a plastic layer disposed over and conforming to the base body of the dispensing cartridge. The plastic layer has a stepped section arranged between the gripping area and the plateau area that prevents the base body of the dispensing cartridge from rotating.

BRIEF DESCRIPTION OF THE DRAWINGS

The dispensing cartridge and package of the disclosure will be described below with reference to the drawings based on two preferred embodiments. The drawings show.

DETAILED DESCRIPTION OF ILLUSTRATIVE EMBODIMENTS

Another aspect of the present disclosure is to create a protective package impervious to germs for a dispensing cartridge described above, in which such a dispensing cartridge with a plurality of tacking nails accommodated therein can be transported in a sterile manner.

The dispensing cartridge according to the disclosure exhibits a base body preferably comprised of medical-grade plastic or even metal, which as viewed from above preferably exhibits a circular shape, and whose one half is configured as a deeper lying gripping surface preferably provided with knobs. Adjacent thereto is a plateau-shaped area, in which three grooves are preferably incorporated, which outwardly extend in a radial direction from the center of the plateau area at an angle of preferably 35° or even 45° relative to each other. The base of each groove incorporates a slotted opening, i.e., a receiving slot, which has a width slightly larger than the diameter of the nail shank. Formed in turn underneath the slotted opening is an underlying section that expands relative to the latter, which incorporates the expanded arrowhead-like area of the tacking nails when the latter are being inserted into the receiving siot. The slotted opening here has a width slightly smaller than the diameter of a nail shank, so that the nail shank is fixedly clamped in the slotted opening owing to the resilient characteristics of the medical-grade plastic material. Below the plateau area, the base body has a support area, with which the base body can support itself on a support surface while exerting a compressive force on the nail head of a tacking nail inserted into the slotted opening.

The advantage to the dispensing cartridge of the disclosure is that several tacking nails can be provisioned in the slotted openings along a row in a reliable manner and secured against inadvertently falling out, so as to be directly removed by a positioning instrument, without there being a risk that the nail heads or nail shanks can come into contact with contaminating surfaces during transport. Another advantage is that the dispensing cartridge can be ergonomically gripped with one hand by the dentist via its base body divided into a gripping area and a plateau area, and its bottom side can be placed on a surface for removing a nail by means of a positioning instrument held in the other hand if needed, so as to press the positioning instrument in a targeted manner against a nail head at a high pressure without the risk of it sliding off. In this case as well, the special configuration always ensures that the removed tacking nails are sterile.

Figure 1:
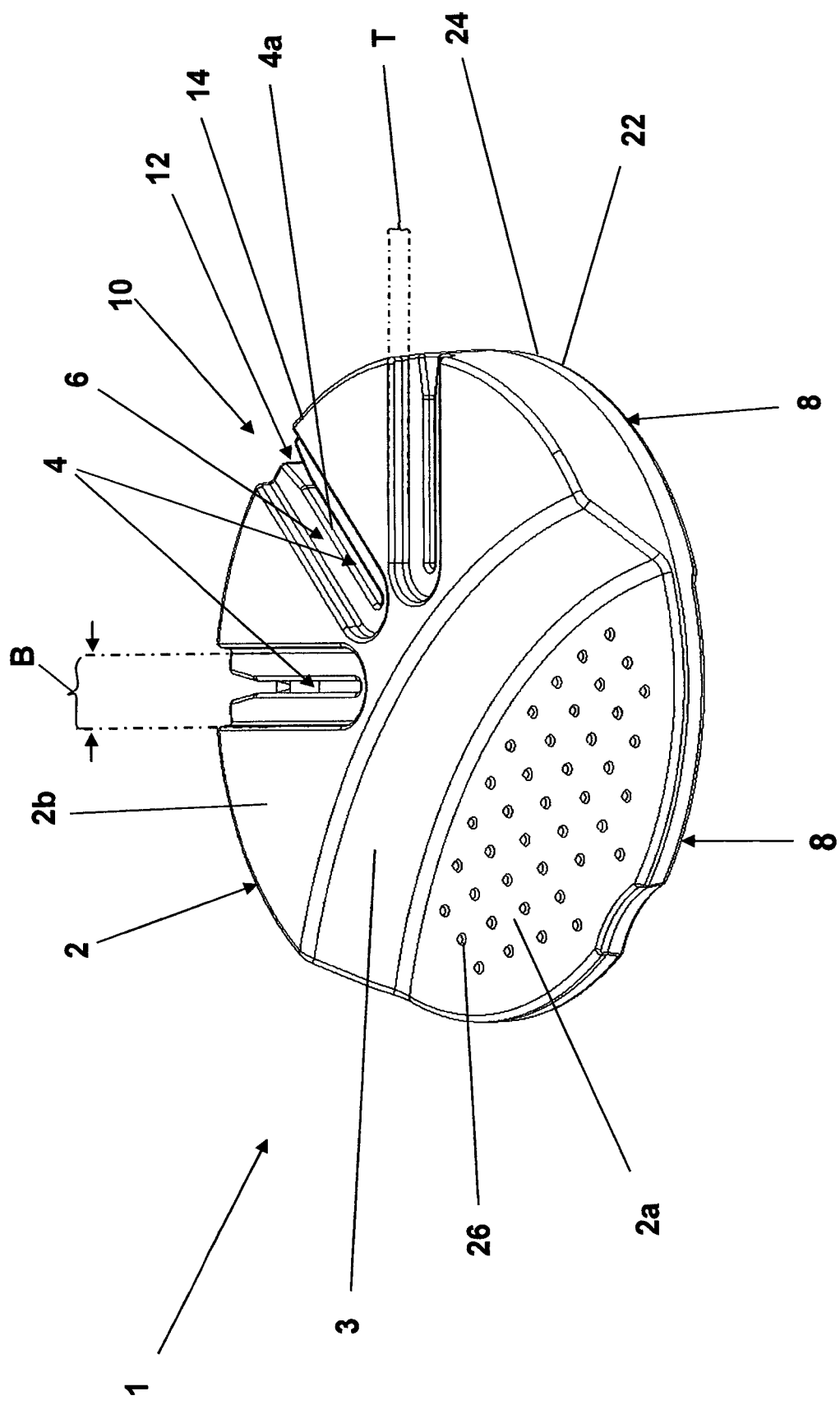
FIG. 1 shows a spatial oblique view of the top side of a first embodiment of the dispensing cartridge according to the disclosure, with a slotted opening continuous toward the edge.
Figure 6:
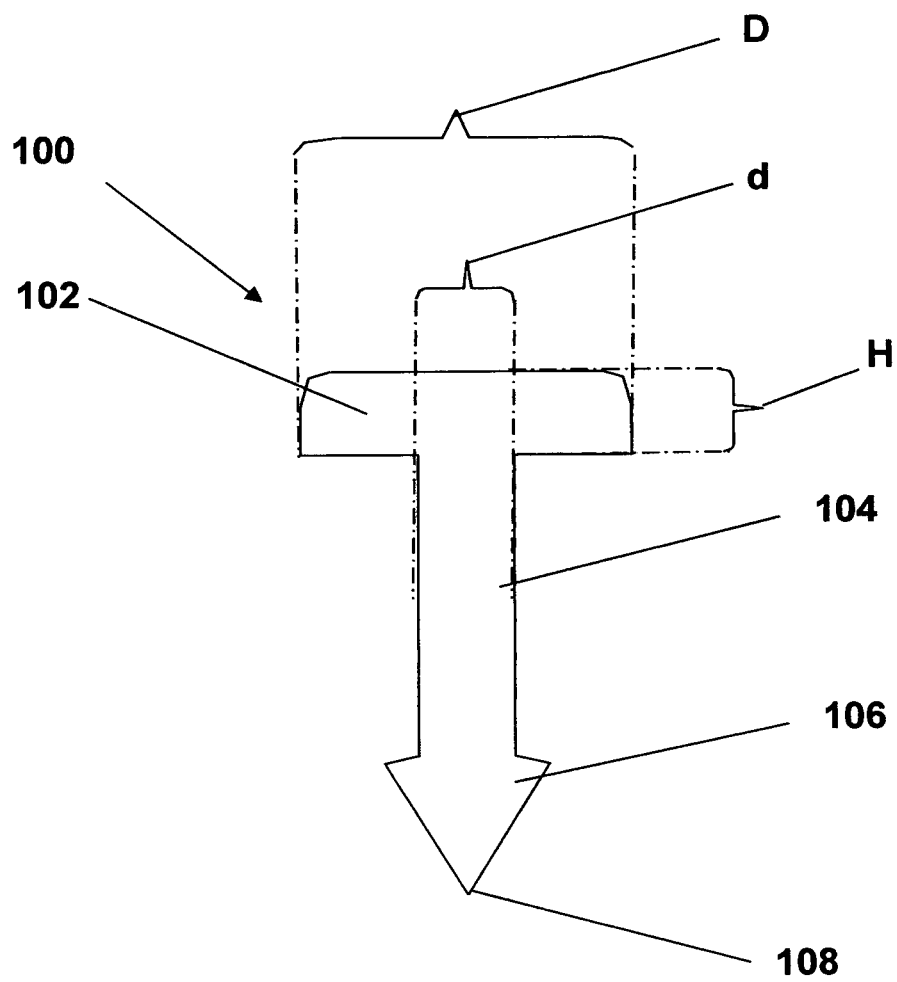
FIG. 6 shows a schematic side view of a tacking nail to be accommodated in a dispensing cartridge according to the disclosure.

As shown in FIG. 1, a dispensing cartridge 1 for a tacking nail 100 depicted in FIG. 6 encompasses a base body 2, in which at least one, but preferably at least three slotted openings 4 are formed, into which the nails 100 can be inserted with their nail shank 104. As may further be gleaned from the illustration in FIG. 6, each tacking nail 100 has an expanded nail head 102 with a diameter D and a height H, a nail shank 104 extending away from the nail head 102 with a diameter d and an expanded arrowhead-like area 106 adjacent thereto, which tapers to a tip 108, and acts as a barb once the nail 100 has been driven into a bone (not shown in any greater detail).

According to the illustrations in FIGS. 1 to 5, the base body 2 has a gripping area 2a and a plateau area 2b adjacent thereto, between which is arranged a transitional surface 3 inclined at an angle, for example of 45°, which serves as a support and contact surface for a human thumb when the base body 2 is held between the thumb and forefinger while using the dispensing cartridge 1. The transitional surface 3 preferably has an arcuate configuration as shown in FIG. 1, and advantageously increases gripping security. In addition, torques, for example those generated by a compressive force exerted transverse to the slotted opening while accommodating a nail 100, are advantageously introduced into the thumb surface, which reduces the risk of an inadvertent lateral pivoting or sliding by the base body.

Each of the slotted openings 4 formed in the plateau area 2b has a width b (see FIG. 2) that is slightly smaller than the diameter d of a nail shank 104, so that the nail shank 104 of a tacking nail 100 is fixedly clamped in its slotted opening 4 after introduced into the latter. For purposes of linguistic simplification, aspects of the disclosure will in the following be described referring only to a single slotted opening.

Formed on the top side of the preferably flatly configured plateau area 2b and extending on either side of the slotted opening 4 is a grooved depression 6, whose depth T exceeds the height H of the nail head 102 and whose width B exceeds the diameter D of the nail head 102. Further arranged underneath the plateau area 2b is a support area 8, against which the base body 2 is supported when a compressive force is applied to the nail head 102 of a tacking nail 100 inserted into the slotted opening 4.

Figure 2:
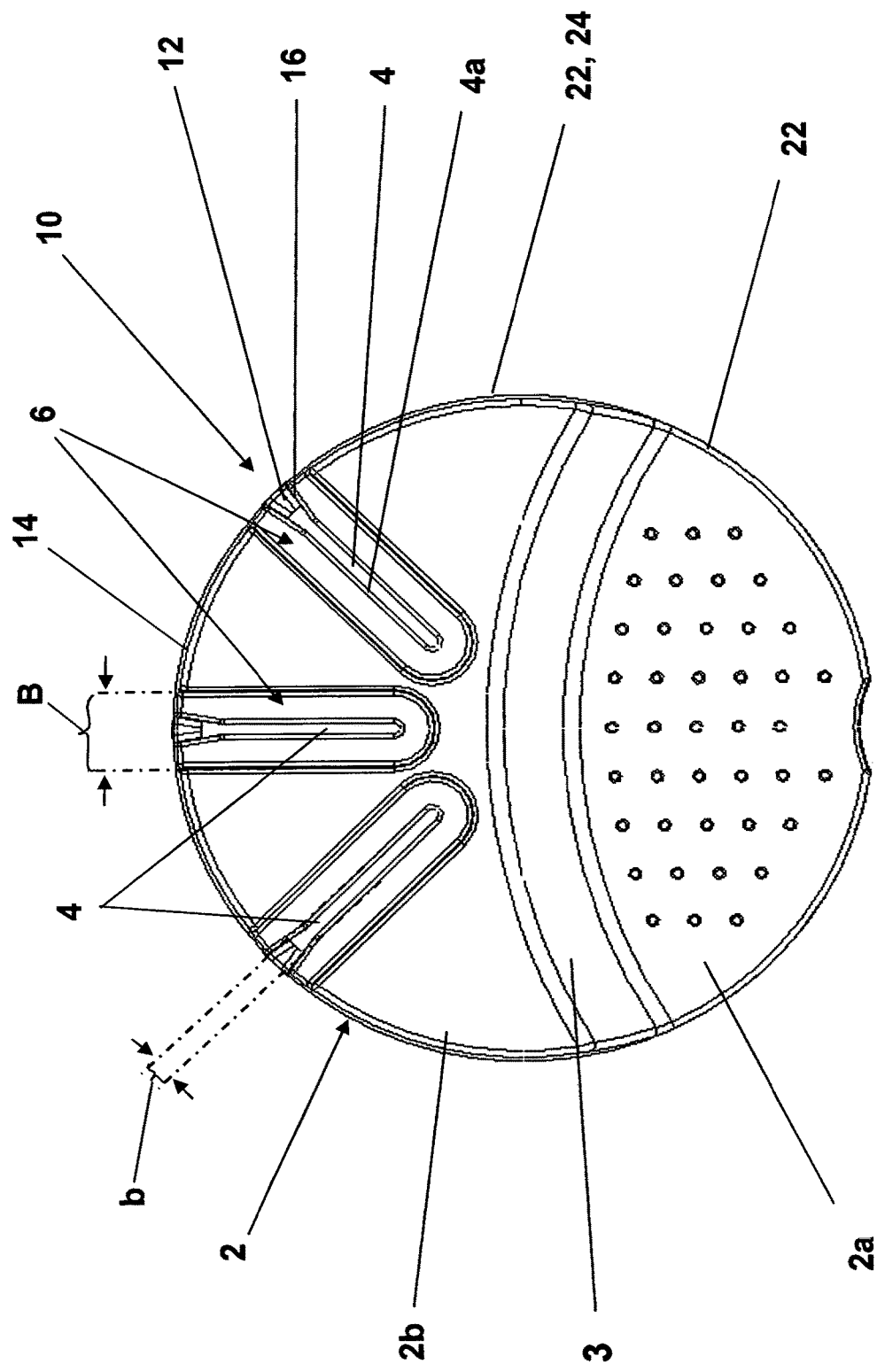
FIG. 2 shows a top view of the dispensing cartridge in FIG. 1.
Figure 3:
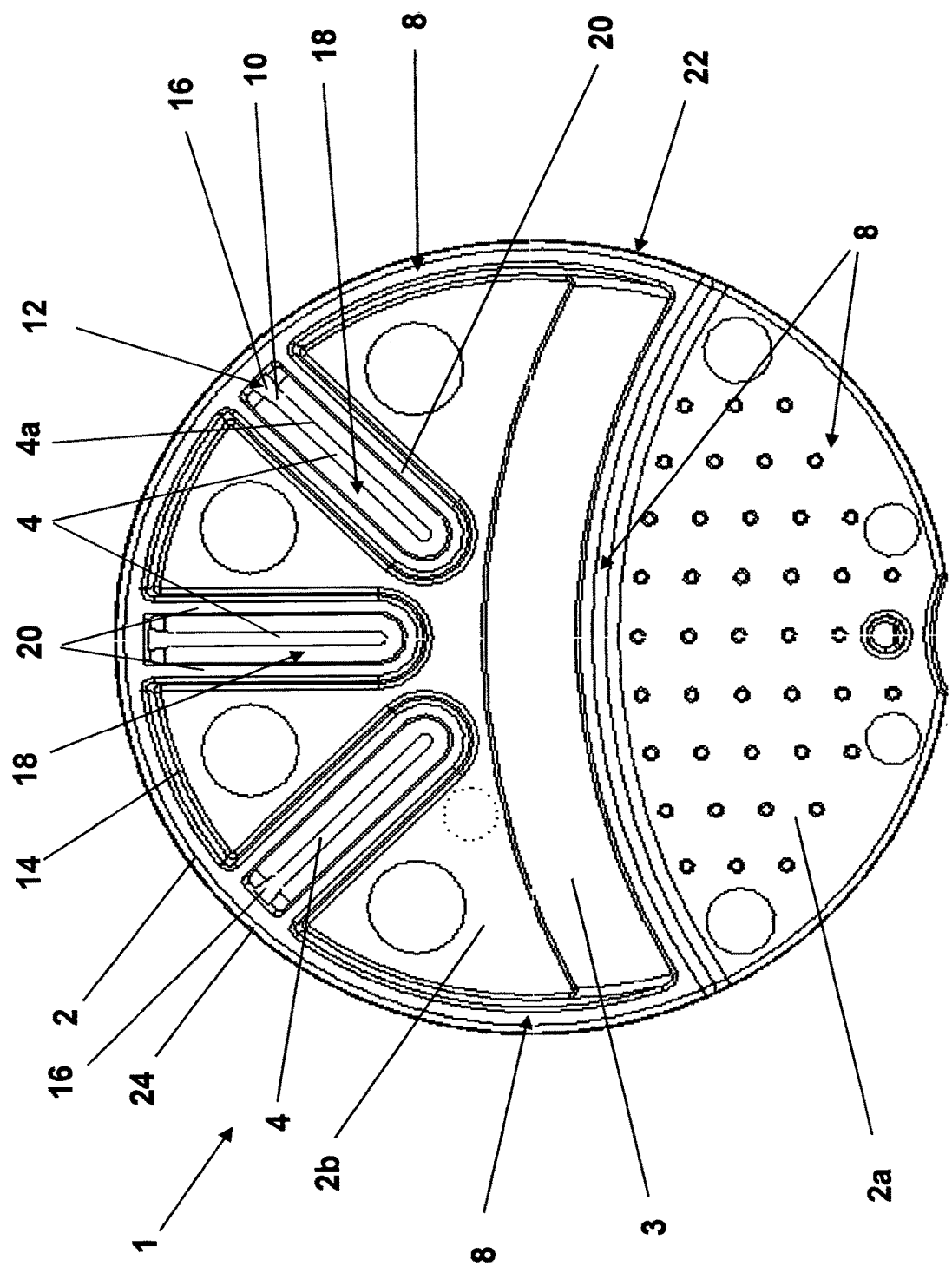
FIG. 3 shows a schematic spatial view of the bottom side of the embodiment in FIG. 1.

As may be gleaned from the illustration in FIGS. 1 to 3, the wall surface 4a of the slotted opening 4 in a first embodiment of the dispensing cartridge 1 according to the disclosure exhibits a frontal opening 12 in the area of an edge-side end 10 of the slotted opening 4, through which a tacking nail 100, after gripped by a positioning instrument along the slotted opening 4, can be moved out of the latter, and removed from the base body 2 over the lateral edge 14 of the plateau area 2b.

In order to here facilitate the removal as well as the introduction of the tacking nails 100 from the edge-side end 10 into the frontal opening 12, the slotted opening 4 opens like a mouth in the area of the frontal opening 12.

Figure 4:
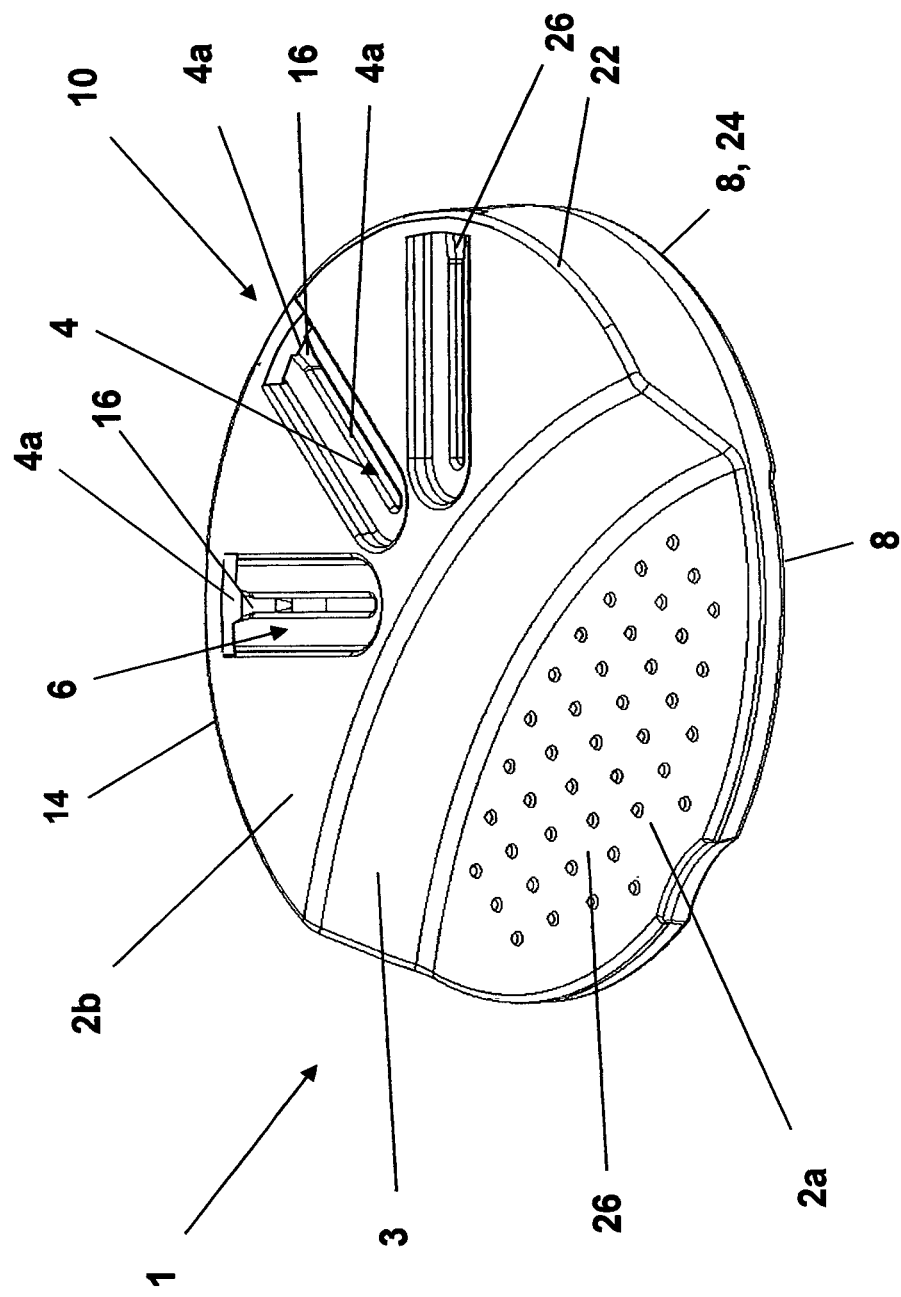
FIG. 4 shows a spatial oblique view of the top side of a second embodiment of the dispensing cartridge according to the disclosure, with a slotted opening not continuous toward the edge.

In another embodiment depicted in FIG. 4, the slotted opening 4 can alternatively be bordered by a continuously peripheral wall surface 4a, which serves as a stop, and prevents a tacking nail 100 from laterally moving radially outward after gripped with a positioning Instrument. To be able to remove the tacking nail 100, the slotted opening 4 in this embodiment of the disclosure exhibits an expanded section 16 in the area of its edge-side end 10, whose diameter is smaller than the diameter of a nail head 102 and larger than the diameter of the arrowheadlike area 106, so that a tacking nail 100, after gripped with a positioning Instrument, must initially be linearly displaced along the slotted opening 4 up to the wall surface 4a acting as a stop before the latter can subsequently be pulled out of the slotted opening in an upward direction through the expanded section 16. By comparison to the embodiment described above in FIGS. 1 to 3, this provides an added safeguard against a sliding out by the nails, or against the risk of injuries that arise when a tacking nail, after clamped or jammed in the slotted opening, is uncontrollably moved out of the latter by the positioning instrument while exposed to a higher level of force, and in the process comes into contact with a body part, for example, such as a finger of the user.

In another aspect of the disclosure, the two embodiments described above can have a receiving section 18 formed underneath the slotted opening 4 for the expanded arrowhead-like areas 106 of the tacking nails 100 in the base body 2, which, as depicted in FIG. 3, is bordered by lateral protective walls 20. The latter extend away from the bottom side of the slotted opening 4 in the direction toward the support area 8 of the base body 2, until over the tip of a tacking nail 100 accommodated in the slotted opening 4, yielding the advantage that the nail shanks 104 and tips 108 of the tacking nails 100 cannot come into contact with body parts, in particular with the fingers, when gripping the dispensing cartridge 1 on the bottom side of the plateau area 2*b*. In terms of a high process quality and short cycle times in the process of injection molding the plastic material from which the base body 2 is preferably fabricated, it is here especially advantageous if the lateral protective walls 20 of the receiving section 18 extend up until the support area 8, and simultaneously serve as support walls, by way of which a compressive force exerted on the head 102 of a tacking nail 100 is introduced into the support area 8. This is justified by the fact that the liquid plastic material cools significantly faster and more uniformly after injected into an accompanying injection mold. In addition, it is possible to make the entire bottom side of the base body 2 out of solid plastic material or even metal, and only mold, in particular mill, the slotted openings 4, grooved depressions 6 and receiving sections 18 out of solid material. As an alternative to injection molding, it is likewise possible to manufacture the base body 2 as a CAD/CAM component out of medical-grade plastic via rapid prototyping or three-dimensional printing, to which end the base body is constructed by incrementally joining together material points preferably of the support area.

In a preferred embodiment, however, the base body 2 is fabricated in a known manner as an injection molded part out of medical-grade plastic via injection molding, wherein the advantage to shaping the base body in this manner is that the injection molds used for this purpose exhibit no undercuts that require additional sliders, which must be moved in and out of the injection mold in a complicated manner during each injection molding process.

As may further be gleaned from the illustrations in FIGS. 1 to 5, the plateau area 2*b* is elevated relative to the gripping area 2*a*, wherein the height difference between the top side of the plateau area 2*b* and top side of the gripping area 2*a* given a base body with a diameter of 30 mm can measure 3 to 6 mm, for example. In terms of having the base body be reliably supported while removing a tacking nail, it is especially advantageous that the support area 8 on the bottom side of the gripping area 2*a* extend along a plane over the entire gripping area and plateau area 2*b*.

As further shown by the illustrations in FIGS. 1-5, the area of the outer edge 22 of the base body 2 underneath the plateau area 2*b* has a continuous peripheral outer wall section 24, which preferably directly adjoins the gripping area 2*a* and forms a part of the support area 8, which supports the plateau area 2*b* when the base body 2 rests on a flat substrate.

In order to further enhance gripping safety when holding the base body 2 between the thumb and forefinger with a positioning device to remove a tacking nail 100, knob-like, in particular dome-shaped or even wavy elevations 26 are applied to the top side and/or bottom side of the otherwise flat surfaced gripping area 2*b*, which can have a height of 0.1 to 0.2 mm, and are integrally formed with the plateau area 2*b*.

Finally, as may further be gleaned from the illustrations in FIGS. 1 to 5, the base body 2 preferably exhibits an essentially circular shape as viewed from above, preferably with a diameter of 30 mm. As already mentioned previously, the plateau area 2*b* incorporates a total of three slotted openings 4, which are each lined on either side by a grooved depression 6, and are each angled relative to each other, for example by 35°.

Figure 5:
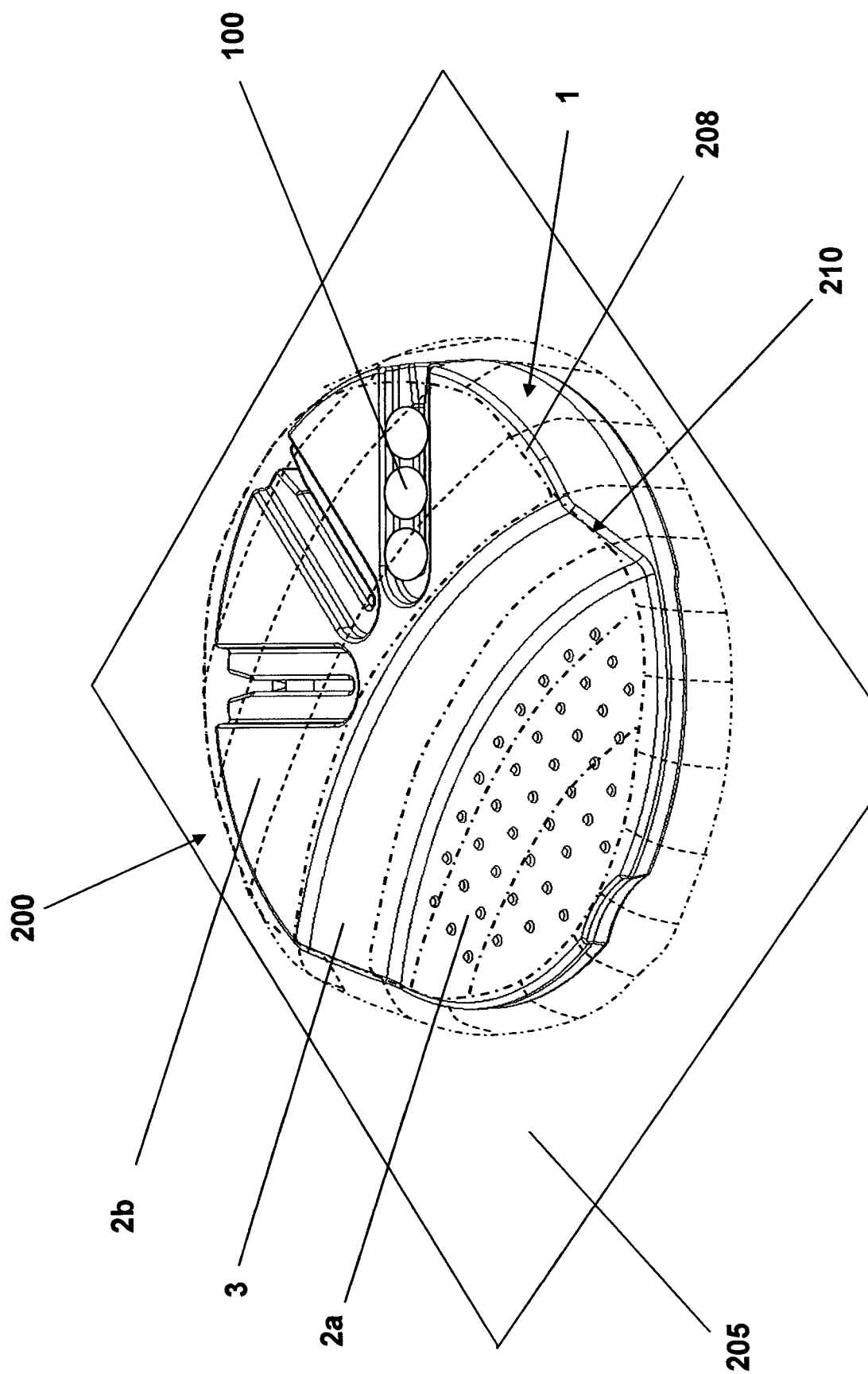
FIG. 5 shows a schematic spatial view of a germ-impervious plastic package with a dispensing cartridge contained therein.

In the Illustration in FIG. 5, the dispensing cartridge 1 according to the disclosure with the tacking nails 100 incorporated therein, of which three tacking nails are presented on the Illustration by example, is accommodated for transport in a plastic package 200 that is impervious to germs and preferably resistant to gamma rays. The plastic package 200 here exhibits a flat base 205, on which rests the bottom side of the base body 2. The flat base 205 can consist of plastic material or also of laminated paper or the like, for example, and have applied to it a dome-like layer 208 made out of preferably transparent, thin-walled plastic material, whose shape is adapted to the that of the top side of the base body 2, which in the area of the transitional surface 3 of the base body 2 extending between the gripping area 2*a* and the plateau area 2*b* has a stepped section 210, which prevents the base body 2 accommodated in the plastic package 200 from rotating.

The invention claimed is:

1. A dispensing cartridge for holding one or more tacking nails for attaching medical-grade films to bones, wherein each tacking nail includes an expanded nail head and a nail shank extending away from the nail head, the nail shank having an expanded lower portion, the dispensing cartridge comprising:
    a base body in which at least one slotted opening is formed and into which the nail shank of a tacking nail may be inserted, wherein the base body has a gripping area and a plateau area adjacent thereto, wherein the slotted opening is formed in the plateau area wherein a grooved depression extending on either side of the slotted opening is formed on a top side of the plateau area; and
    a support area disposed underneath the plateau area and against which the base body is supported when a compressive force is applied to the nail head of the tacking nail that has been inserted into the slotted opening; and
    wherein the base body has a receiving section for receiving the lower portion of a tacking nail, the receiving section being disposed underneath the slotted opening in the base body and being bordered by lateral protective walls, which extend in a direction toward the support area of the base body, the lateral protective walls extending away from a bottom side of the slotted opening.

2. The dispensing cartridge according to claim 1, wherein a wall surface of the slotted opening has a frontal opening at an edge-side end of the slotted opening, through which a tacking nail may be moved out of the slotted opening and removed from the base body.

3. The dispensing cartridge according to claim 2, wherein the slotted opening expands like a mouth in the area of the frontal opening.

4. The dispensing cartridge according to claim 1, wherein the slotted opening is bordered by a continuously peripheral wall surface, wherein the slotted opening has an expanded section at an edge-side end of the slotted opening, thereby permitting a tacking nail to be linearly displaced along the slotted opening up to the expanded section and be pulled out of the base body in an upward direction through the expanded section.

5. The dispensing cartridge according to claim 1, wherein the lateral protective walls of the receiving section extend to the support area and serve as support walls, by way of which a compressive force exerted on the head of a tacking nail is introduced into the support area.

6. The dispensing cartridge according to claim 1, wherein the base body is an injection molded part comprised of medical-grade plastic.

7. The dispensing cartridge according to claim 1, wherein the base body is a CAD/CAM component comprised of medical-grade plastic, or a rapid-prototyping component comprised of medical-grade plastic.

8. The dispensing cartridge according to claim 1, wherein the plateau area is elevated relative to the gripping area, and wherein the support area extends on a bottom side of the base body, over the gripping area and the plateau area.

9. The dispensing cartridge according to claim 1, wherein the support area comprises a peripheral outer wall section adjoining the gripping area that supports the plateau area when the base body rests on a flat substrate.

10. The dispensing cartridge according to claim 1, wherein the top side and/or bottom side of the gripping area is provided with knoblike or wavy elevations.

11. The dispensing cartridge according to claim 1, wherein the base body has a generally circular shape as viewed from above, and wherein the plateau area has a total of three slotted openings, which are each lined on either side by a grooved depression.

12. A plastic package that is impervious to germs and resistant to gamma rays, comprising:
the dispensing cartridge according to claim 1, and
a plastic layer disposed over and conforming to the base body of the dispensing cartridge, the plastic layer having a stepped section arranged between the gripping area and the plateau area that prevents the base body of the dispensing cartridge from rotating.

13. The plastic package of claim 12, further comprising a planar base upon which the dispensing cartridge is disposed.

14. The plastic package of claim 12, wherein the plastic layer is transparent.

15. The plastic package of claim 12, further comprising a plurality of the tacking nails having their nail shanks disposed in the slotted opening in the dispensing cartridge;
wherein the slotted opening has a width that is smaller than a diameter of each of the nail shanks, so that the nail shanks may be fixedly clamped in the slotted opening;
wherein the grooved depression has a depth that is greater than a height of each of the nail heads and a width that is greater than a diameter of each of the nail heads; and
wherein the lateral protective walls extend beyond free ends of the nail shanks.

16. The plastic package of claim 15, wherein the slotted opening in the dispensing cartridge is bordered by a continuously peripheral wall surface; and
wherein the slotted opening has an expanded section at an edge-side end of the slotted opening, and wherein a diameter of the expanded section is smaller than the diameter of each of the nail heads and larger than a diameter of the expanded lower portions of the nail shanks, so that the tacking nails may be linearly moved along the slotted opening to the expanded section, where they may then be pulled out of the base body in an upward direction through the expanded section.

17. In combination, the dispensing cartridge according to claim 1 and a plurality of the tacking nails having their nail shanks disposed in the slotted opening of the dispensing cartridge;
wherein the slotted opening has a width that is smaller than a diameter of each of the nail shanks, so that the nail shanks may be fixedly clamped in the slotted opening;
wherein the grooved depression has a depth that is greater than a height of each of the nail heads and a width that is greater than a diameter of each of the nail heads; and
wherein the lateral protective walls extend beyond free ends of the nail shanks.

\* \* \* \* \*

UNITED STATES PATENT AND TRADEMARK OFFICE
CERTIFICATE OF CORRECTION

PATENT NO. : 10,736,708 B2  
APPLICATION NO. : 15/772283  
DATED : August 11, 2020  
INVENTOR(S) : Geraldine Schultz Page 1 of 1

It is certified that error appears in the above-identified patent and that said Letters Patent is hereby corrected as shown below:

On the Title Page

In Item (71), delete "Rodenbacher Chaussee 4" and insert therefor: --Dentsply Implants Manufacturing GmbH--

Signed and Sealed this
Twenty-ninth Day of September, 2020

Andrei Iancu
*Director of the United States Patent and Trademark Office*